United States Patent
Albrecht et al.

(10) Patent No.: US 7,354,599 B2
(45) Date of Patent: Apr. 8, 2008

(54) LIPOSOMAL FORMULATIONS OF HYDROPHOBIC PHOTOSENSITIZER FOR PHOTODYNAMIC THERAPY

(75) Inventors: Volker Albrecht, Jena (DE); Alfred Fahr, Cölbe/Marburg (DE); Dietrich Scheglmann, Jena-Cospeda (DE); Susanna Gräfe, Jena (DE); Wolfgang Neuberger, F.T. Labuan (MY)

(73) Assignee: CeramOptec Industries, Inc., East Longmeadow, MA (US)

( * ) Notice: Subject to any disclaimer, the term of this patent is extended or adjusted under 35 U.S.C. 154(b) by 0 days.

(21) Appl. No.: 11/298,729

(22) Filed: Dec. 9, 2005

(65) Prior Publication Data

US 2006/0088584 A1    Apr. 27, 2006

Related U.S. Application Data

(62) Division of application No. 10/648,168, filed on Aug. 26, 2003.

(51) Int. Cl.
*A61K 9/127* (2006.01)
(52) U.S. Cl. .................. 424/450; 424/489
(58) Field of Classification Search .............. None
See application file for complete search history.

(56) References Cited

U.S. PATENT DOCUMENTS

| | | | | |
|---|---|---|---|---|
| 5,190,761 A | * | 3/1993 | Liburdy | 424/450 |
| 5,389,378 A | * | 2/1995 | Madden | 424/450 |
| 5,773,027 A | * | 6/1998 | Bergeron et al. | 424/450 |
| 6,074,666 A | | 6/2000 | Desai et al. | |
| 6,440,950 B1 | * | 8/2002 | Zeimer | 514/63 |
| 6,498,945 B1 | * | 12/2002 | Alfheim et al. | 600/407 |
| 2005/0107329 A1 | | 5/2005 | Desai et al. | |

OTHER PUBLICATIONS

Harris and Chess, "Effect of Peguylation on Pharmaceuticals," Nature, Mar. 2003, vol. 2, pp. 214-221.
Mody, "Pharmaceutical development and medical applications of porphyrin-type macrocycles," Journal of Porphyrins and Phth. Vo. 4, 362-367.
Storn and Crommelin, "Liposomes: quo vadis?" PSTT, vol. 1, No. 1, Apr. 1998, 19 to 31.

* cited by examiner

*Primary Examiner*—Gollamudi S. Kishore
(74) *Attorney, Agent, or Firm*—Bolesh J. Skutnik; B J Associates

(57) ABSTRACT

Pharmaceutical liposomal formulations are described for photodynamic therapy comprising a, hydrophobic porphyrin photosensitizer, a monosaccharide and one or more synthetic phospholipids, which are stable in storage especially through freeze-drying process. The liposomal formulations provide therapeutically effective amounts of the photosensitizer for intravenous administration. In particular derivatives of chlorins and bacteriochlorins, such as temoporfin, are, hydrophobic photosensitizers whose efficacy and safety are enhanced by such liposomal formulations. The formulation can be efficiently freeze-dried preserving the size of the liposomal vehicles, and the content of a therapeutically effective amount of the photosensitizer, due to the selection of phospholipids and monosaccharides. The invention also relates to liposome compositions formed upon reconstitution with an aqueous vehicle. The freeze-dried formulation upon reconstitution with a suitable aqueous vehicle forms liposomes that are useful for intravenous administration.

6 Claims, 2 Drawing Sheets

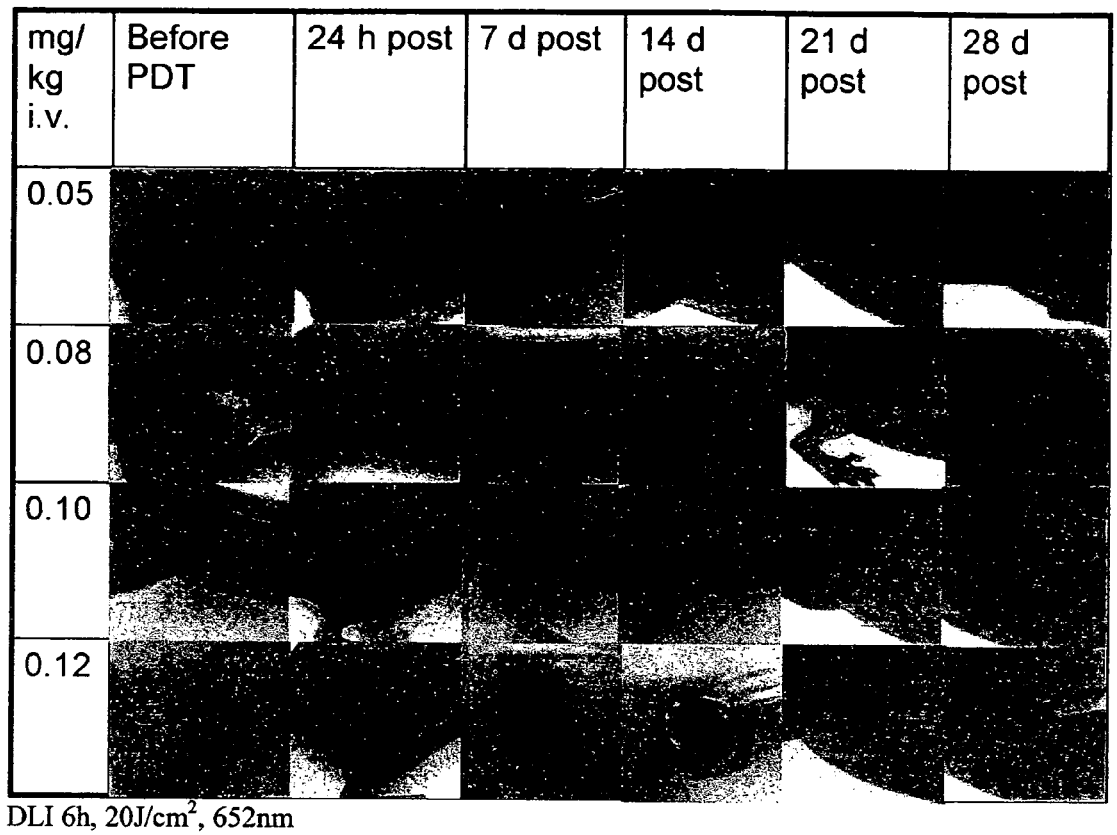
DLI 6h, 20J/cm², 652nm
Figure 3
Figure 4
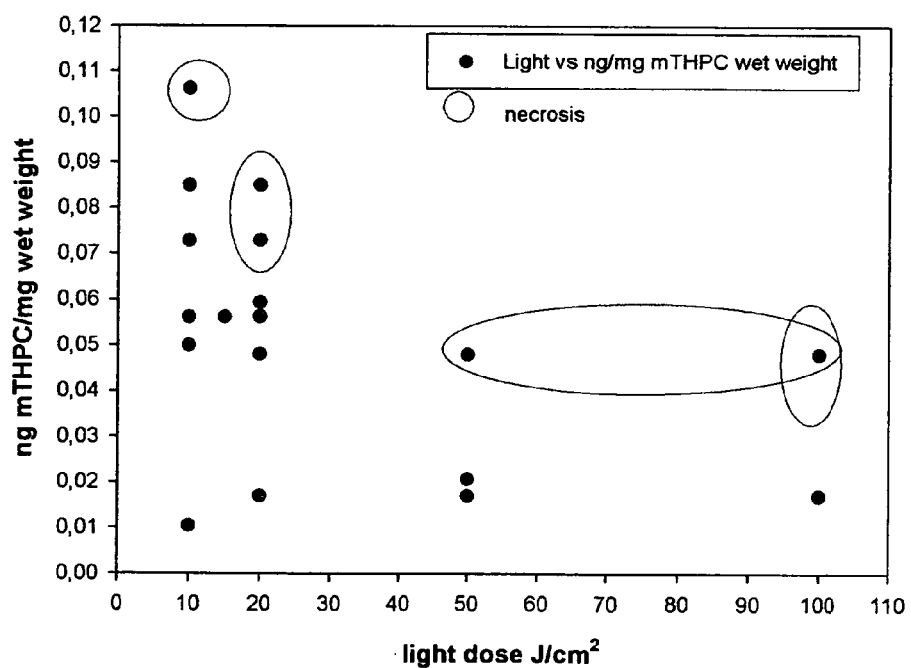

LIPOSOMAL FORMULATIONS OF HYDROPHOBIC PHOTOSENSITIZER FOR PHOTODYNAMIC THERAPY

REFERENCE TO RELATED CASE

This application is a continuation and divisional of co-pending U.S. patent application Ser. No. 10/648,168 filed on Aug. 26, 2003 by Volker Albrecht et al., inventors, entitled "Non-polar Photosensitizer formulations for PhotoDynamic Therapy", and incorporated by reference herein.

BACKGROUND OF THE INVENTION

1. Field of the Invention

The present invention concerns the preparation of liposomal formulations containing Temoporfin or other hydrophobic, photosensitizers and their use in therapy, particularly using intravenous injection.

2. Information Disclosure Statement

Liposomes are artificial vesicles composed of concentric lipid bilayers separated by water-compartments and have been extensively investigated as drug delivery vehicles. Due to their structure, chemical composition and colloidal size, all of which can be well controlled by preparation methods, liposomes exhibit several properties which may be useful in various applications. The most important properties are colloidal size, i.e. rather uniform particle size distributions in the range from 20 nm to 10 μm, and special membrane and surface characteristics.

Liposomes are used as carriers for drugs and antigens because they can serve several different purposes (Storm & Crommelin, Pharmaceutical Science & Technology Today, 1, 19-31 1998). Liposome encapsulated drugs are inaccessible to metabolizing enzymes. Conversely, body components (such as erythrocytes or tissues at the injection site) are not directly exposed to the full dose of the drug. The Duration of drug action can be prolonged by liposomes because of a slower release of the drug in the body. Liposomes possessing a direction potential, that means, targeting options change the distribution of the drug over the body. Cells use endocytosis or phagocytosis mechanism to take up liposomes into the cytosol. Furthermore liposomes can protect a drug against degradation (e.g. metabolic degradation). Although sometimes successful, liposomes have limitations. Liposomes not only deliver drugs to diseased tissue, but also rapidly enter the liver, spleen, kidneys and Reticuloendothelial Systems, and leak drugs while in circulation (Harris & Chess, Nature, March 2003, 2, 214-221).

Photodynamic therapy (PDT) is a promising new technique being explored for use in a variety of medical applications and is known as a well-recognized treatment for the destruction of tumors ("Pharmaceutical development and medical applications of porphyrin-type macrocycles", T. D. Mody, J. Porphyrins Phthalocyanines, 4, 362-367 2000). Another possible application of PDT is the treatment of infectious diseases due to pathogenic micro organisms.

A constant problem in the treatment of infectious disease is the lack of specificity of the agents used for the treatment of disease, which results in the patient gaining a new set of maladies from the therapy. Secondly, micro organisms can adapt to negate the effect of most chemically designed antimicrobials creating resistant strains, which require ever more active ingredients to stop their activity.

The use of PDT for the treatment of various types of disease has been limited due to the inherent features of photosensitizers (PS). These have included their high cost, extended retention in the host organism, substantial skin photo toxicity, low solubility in physiological solutions (which also reduces its usefulness for intravascular administration as it can provoke thromboembolic accidents), and low targeting effectiveness. These disadvantages, particularly of PS in the prior art, had led to the administration of very high doses of a photosensitizer, which dramatically increase the possibility of accumulation of the photosensitizer in non-damaged tissues and the accompanying risk of affecting non-damaged sites.

Efforts to reduce cost and to decrease background toxicity have been underway but are unrelated to the developments of the present invention. Work to improve solubility in physiological solutions, effects of skin photo toxicity, retention in host organism and to a lesser extent targeting effectiveness are the areas where the present invention provides new and non-obvious improvements on the use of PDT to treat various hyperplasia and related diseases.

Desai et al. (U.S. Pat. No. 6,074,666) and a recent publication, US 2005/0107329 also by Desai et al. describe the preparation and use of liposomal formulations incorporating porphyrin photosensitizers, particularly hydro-benzoporphyrins, a disaccharide or polysaccharide and one or more phospholipids. These phospholipids are quite general, but generally included at least one 'natural' phospholipid, e.g. from eggs or soy. The preferred porphyrin photosensitizers are mono-substituted with a benzo-ring connected to one of the four pyrryl rings in the porphyrin. The use of disaccharides or polysaccharides is required along with one or more phospholipids used to make the liposomes. Using the broad range of permitted phospholipids and the di- and poly-saccharides with materials like chlorins, bacteriochlorins, and especially tetra-substituted derivatives of these does not necessarily yield stable liposomes capable of freeze drying and reconstitution.

Since the application of photodynamic therapy in the treatment of cancer and other diseases is increasing rapidly, there is also a bigger demand for new photosensitizer formulations. These new photosensitizer formulations need to be stable, easy to manufacture and to handle.

OBJECTIVES AND BRIEF SUMMARY OF THE INVENTION

It is an object of the present invention to provide an improved photosensitizer formulation for use in photodynamic therapy (PDT).

It is a further object of the present invention to preserve upon reconstitution the structure and size of liposomal constructs with incorporated hydrophobic photosensitizer during and after freeze-drying processes by using monosaccharides as cryoprotectants.

It is another object of the present invention to provide a photosensitizer formulation with improved pharmacokinetic properties and efficacy of PDT.

It is yet another object of the present invention to improve the safety of PDT by achieving better distribution of photosensitizer in diseased tissue over normal tissue.

Briefly stated, the present invention involves pharmaceutical liposomal formulations for photodynamic therapy comprising a hydrophobic porphyrin photosensitizer, a monosaccharide and one or more synthetic phospholipids, which are stable in storage especially through freeze-drying process and reconstitution. The liposomal formulations provide therapeutically effective amounts of the photosensitizer for intravenous administration. In particular derivatives of chlorins and bacteriochlorins, especially temoporfin, are hydrophobic photosensitizers whose efficacy and safety are enhanced by such liposomal formulations. The formulation can be efficiently freeze-dried preserving the size of the liposomal vehicles, and the content of a therapeutically effective amount of the hydrophobic photosensitizer, due to the selection of phospholipids and monosaccharides. The invention also relates to liposome compositions formed upon reconstitution with an aqueous vehicle. The freeze-dried formulation upon reconstitution with a suitable aqueous vehicle forms liposomes that are useful for intravenous administration.

The above, and other objects, features and advantages of the present invention will become apparent from the following description read in conjunction with the accompanying figures.

BRIEF DESCRIPTION OF FIGURES

FIG. 3 shows pictures of 24 hours prior and 1, 2, 3 and 4 weeks post PDT treatment effect in the mice tumor injected with liposomal formulation of mTHPC dose 0.05, 0.08, 0.10 and 0.12 mg/kg.

FIG. 4 shows the correlation of drug dose in the tissue and efficacy of photodynamic therapy.

DETAILED DESCRIPTION OF PREFERRED EMBODIMENTS

Figure 1:
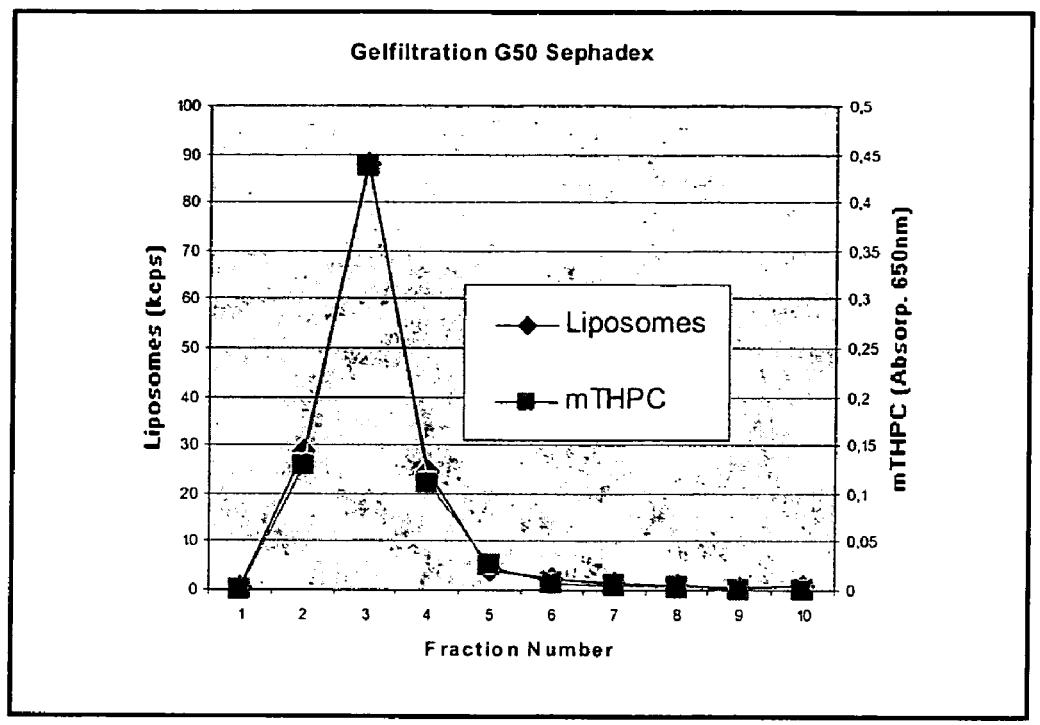
FIG. 1 is a gel filtration curve of liposomal formulated mTHPC. Both, lipid components and mTHPC show the same distribution over all fractions collected. Related data for this figure appears in Tables 1 and 2.

In Desai et al., without the polysaccharides, including disaccharides, the formulations given there are not stable to freeze-drying, and reconstitution. Without this protection the lumen within the liposome is quite unstable and often on reconstitution the liposomes tend to clump together providing unstable sizes over a wide range of dimensions. These problems lead to reconstituted formulations which may be particularly poor for systemic application as well as local injection.

As described here, pharmaceutical liposomal formulations for PDT applications, which have commercially useful extended shelf lives, are presented. They comprise a hydrophobic photosensitizer, synthetic phospholipids and a monosaccharide. The hydrophobic photosensitizer is preferably selected from chlorins, bacteriochlorins and other di- and tetra-hydroporphyrins that have light absorption maxima in the range of 640-780 nm.

Preferred synthetic phospholipids are phosphatidyl cholines, such as dipalmitoylphosphatidy choline (DPPC), dimyristoyl phosphatidyl choline (DMPC), Distearoyl phosphatidyl choline (DSPC), and phosphatidyl glycerols such as dipalmitoyl glycerol (DPPG) and dimyristoyl phosphatidyl glycerol (DMPG). Most preferred synthetic phospholipids are DPPC and DPPG. Preferred monosaccharides are glucose or fructose.

Liposomal formulation of this invention may be generally prepared by dissolving the selected hydrophobic photosensitizer and selected synthetic phospholipids in a suitable alcoholic solvent, which may contain other organics such as chloroform. The resulting solution is dried under vacuum to evaporate the alcoholic solvent, or otherwise treated to remove substantially all the solvent. The solid residue obtained is taken up in a monosaccharide solution and homogenized. For many applications the solution is usually then freeze dried for storage. It is reconstituted in an aqueous solution containing monosaccharides for administration. Alternatively, especially for highly dilute liposomal formulations, the initial homogenized solution is simply diluted with additional monosaccharide solution.

In the liposomal formulations, the hydrophobic photosensitizers is contained within the lipid bilayer membrane. These liposomal formulations are found to improve efficacy and reduce toxicity when compared to conventional alcoholic-based formulations. In particular liposomal formulations of m-tetrahydroxyphenylchlorin (mTHPC) show enhanced pharmacokinetics and biodistribution when compared to the conventional alcoholic formulation of mTHPC.

As noted earlier, these liposomal formulations have commercially valuable shelf lives even without freeze drying which is aided by the processing used to make the formulations. The shelf life can generally be enhanced by freeze drying them for extended storage and reconstituting them just prior to administration, wherein the presence of the monosaccharide is particularly of value.

The photosensitizing liposomal formulations are useful to target the hydrophobic photosensitizer molecule to the unwanted cells or tissues or other undesirable materials and, after irradiation with an appropriated light source, to damage the target. The photosensitizing formulations are also useful to locate unwanted cells or tissues or other undesirable materials by using fluorescence imaging methods with generally ultraviolet absorbed wavelengths to generate visible fluorescence. The imaging can be done without or in conjunction with photochemical activation of the photosensitizer, by irradiations generally of visible or near infrared wavelengths.

The liposomal formulations of the invention are especially useful to transport hydrophobic photosensitizers. Hydrophobic substances are integrated within the membrane of the vehicles, a structure that is accessible to targeted cells, freeing the photosensitizer for action directly to the cell membrane. This mechanism delivers the photosensitizer directly to the cellular membrane system, one preferred place of action. Thus the photosensitizer, being effectively activated by illumination with an appropriate external light source, can irreversibly damage unwanted cells, tissues or other structures.

Conventionally constructed liposomal formulations are normally used to transport compounds trapped into the luminal part of the vehicle. Here the focus is on a different transport compartment, one where the photosensitizer resides within the membrane.

The combination of monosaccharide, as e.g. glucose or fructose, and the photosensitizer attached to phospholipids is an excellent tool to preserve the size of the liposomes during freeze-drying and reconstitution using a physiological common carbohydrate instead of disaccharides. This benefits parenteral liposomal applications, as glucose levels in blood are high and controlled well physiologically, addition of small amounts of glucose to the blood stream are well tolerated by the human body.

EXAMPLE 1

Preparation of Liposomes Containing m-THPC mTHPC (Temoporfin) was synthesized as described in U.S. Pat. Nos. 4,992,257 and 5,162,519, incorporated herein by reference.

Liposomes were prepared according to the following general procedure:

Hydrophobic photosensitizer, and typically two or more synthetic phospholipids are dissolved in alcoholic solution. The solution is then dried under vacuum using a rotary evaporator. Water for injection is added to rehydrate the lipid film at a temperature of 50° C. for at least 2 hours. The mixture is then passed through a homogenizer filter system using a final pore size of 100 nanometers. The rehydration water is supplemented with monosaccharides. The filtrate is collected, filled into vials and optionally freeze dried. The freeze dried composition is reconstituted with water for injection prior to administration.

In one of the embodiment of this invention liposomes are prepared in t-butanol solution wherein the hydrophobic photosensitizer and synthetic phospholipids are dissolved in t-butanol. This solution is then dried by evaporation at about room temperature as t-butanol crystallizes at 20° C. The power is dispered in water with monosaccharide and passed through a homogenizer and suitable filter. The filtrate is collected into vial and optionally freezes dried. The freezes dried composition can be reconstituted with water for pararental administration.

Using the foregoing procedure, several different preparations of the liposomal formulation were prepared generally as follows:

EXAMPLE 1

| Ingredient | Amount % w/v |
| --- | --- |
| mTHPC | 0.05 to 0.15 |
| synthetic Phosphatidyl Choline | 0.5 to 2.0 |
| synthetic Phosphatidyl Glycerol | 0.05 to 0.2 |
| Glucose | 2.0 to 12.0 |
| Water for Injection | as required to achieve desired concentrations above |

The Phosphatidyl Choline can be one or more synthetic cholines such as dipalmitoyl phosphatidyl choline (DPPC), dimyristoyl phosphatidyl choline (DMPC), distearoyl phosphatidyl choline (DSPC). Suggested glycerols include dipalmitoyl phosphatidyl glycerol (DPPG) and dimyristoyl phosphatidyl glycerol (DMPG).

A preferred ratio of the phospholipids for choline to glycerol is about 10:1, see example below.

They were found to function well in use according to the present invention.

EXAMPLE 2

Physical and Chemical Stability of Liposomal m-THPC

The physical stability of the liposomal formulations was measured by monitoring the particle size distribution by photon correlation spectroscopy.

| Stability of liposomal mTHPC | |
| --- | --- |
| Storage Conditions | Mean Particle Size distribution (nm) |
| Initial | 166 |
| 23° C.-1 Month | 177 |
| 23° C.-4 Month | 167 |

Another set of specific experiments repeated for separate batches of the m-THPC were followed for a longer period of time are given below. Storage conditions were 25° C. and 60% RH

EXAMPLE 2-1

| Ingredient | Amount mg/ml |
| --- | --- |
| mTHPC | 0.6 |
| synthetic Phosphatidyl Choline | 16.5 |
| synthetic Phosphatidyl Glycerol | 1.65 |
| Glucose | ~5.0 |
| Water for Injection | as required to achieve desired concentrations above |

The reconstituted formulation was evaluated for particle size, zeta potential and retention of active ingredient at the intervals below.

| | Initial | 1 month | 3 months | 6 months | 9 months | 12 months |
| --- | --- | --- | --- | --- | --- | --- |
| Particle size: | 135 | 127 | 130 | 127 | 128 | 131 |
| Zeta-potential | −83.3 | −58.0 | −66.4 | −65.7 | −59.4 | −66.8 |
| m-THPC content | 94.5 | 90.9 | 91.6 | 92.2 | 91.6 | 91.8 |

EXAMPLE 2-2

| Ingredient | Amount mg/ml |
| --- | --- |
| mTHPC | 0.5 |
| synthetic Phosphatidyl Choline | 16.0 |
| synthetic Phosphatidyl Glycerol | 1.60 |
| Glucose | ~5.0 |
| Water for Injection | as required to achieve desired concentrations above |

The reconstituted formulation was evaluated for particle size, Zeta Potential and retention of active ingredient at the intervals below.

| | Initial | 1 month | 3 months | 6 months | 9 months | 12 months |
| --- | --- | --- | --- | --- | --- | --- |
| Particle size: | 119 | 115 | 118 | 115 | 117 | 123 |
| Zeta Potential | −102.7 | −72.3 | −70.7 | −70.1 | −69.8 | −66.9 |
| m-THPC content %: | 94.2 | 91.2 | 93.0 | 93.2 | 91.2 | 92.3 |

EXAMPLE 3

Localization of mTHPC Within the Liposomal Bilayer of the Formulation

Gel filtration of liposomal formulation performed on Sephadex G50 columns. As shown in FIG. 1, lipids and mTHPC show the same distribution over all fractions indicating a physically interaction of both components i.e.

integration of mTHPC into the membrane bilayer. The data related to the FIG. 1 is tabulated in table 1 and 2.

EXAMPLE 4

Pharmacokinetic Properties in Mice

HT29 human colorectal carcinoma cells are used.

Six to eight week old adult female athymic NMRI nu/nu mice weighting 22-24 g were inoculated subcutaneously in the left hind thigh with 0.1 ml of $8 \times 10^7$ HT29 human colorectal cells/ml in 5% glucose. Two to three weeks later, as the tumor reached a surface diameter of 7-8 mm, and a thickness of 2-3 mm in height, 50 µL liposomal formulation of mTHPC (essentially equivalent to that of the earlier examples except that the concentration of mTHPC was 0.04 mg/ml) were injected into lateral tail vein. At a selected time points (0, 1, 2, 3, 4, 5, 6 and 8 hours) post injection, 4 mice at each time point were anesthetized and sacrificed and tissue samples of tumor, skin and skeletal muscle were weighted and stored at −70° C. Briefly after tissue samples were thawed and held on ice, all tissue samples were reduced to small pieces by cutting with a scalpel, were weighed and were freeze dried. The resulting powdered tissue was weighed and approx. 10-20 mg was transferred to a 2.0 ml reaction tube. Then 1.5 ml of methanol:DMSO (3:5, v:v) was added followed by immediate mixing for three times five seconds using a vortex mixer operating at 2,400 rpm and then incubated at 60° C. while continuously shaking for at least 12 hours. All samples were then spun at 16,000 g in a centrifuge for five minutes. 1 ml of each supernatant was transferred to a HPLC vial and analysed by HPLC. The fluorescence was set at 410 nm for excitation and 653 nm for emission. The tissue concentration of mTHPC was calculated from a calibration curve constructed by plotting the peak height values of mTHPC standard solutions versus their concentrations.

Results

No adverse effects were observed during or immediately after injection of liposomal formulation of mTHPC (temoporfin). The subjective quality of each injection was recorded, since the mouse tail vein is quite small and the injection was not always successful. Examination of these data shows that perfect injections were achieved in about 95% of cases with liposomal formulation of mTHPC. In those cases in which the injection was not successful, the animal was excluded from the experiment. In case there were indications of slight extravasation of the drug or slight leakage from the puncture whole, the animal was not excluded, but marked as having received an injection which was not perfect.

Figure 2:
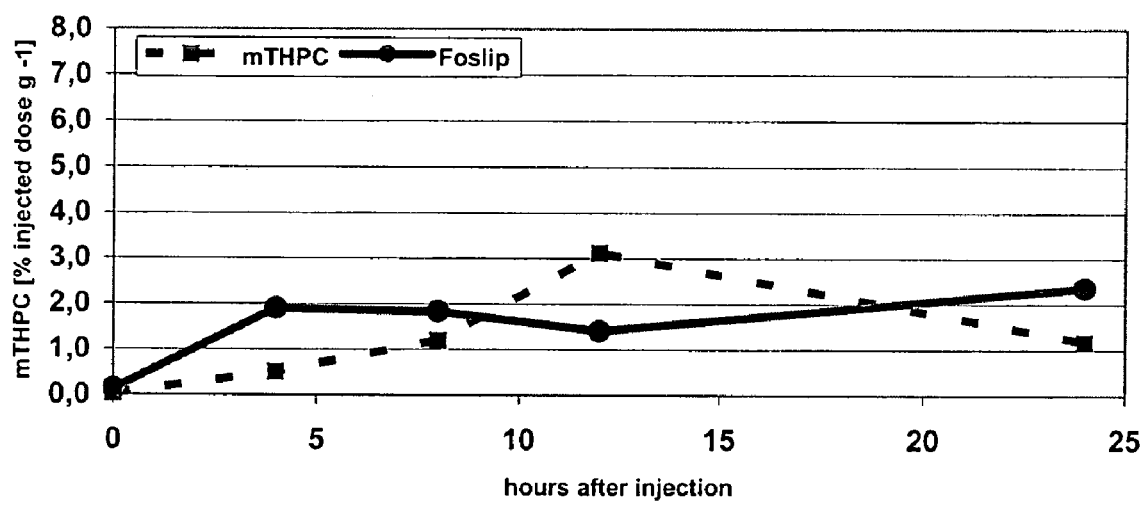
FIG. 2 shows the drug concentration at different hours after intravenous injection of conventional mTHPC and new liposomal Temoporfin.

The results demonstrate that a liposomal temoporfin formulation of the present invention indeed show faster pharmacokinetics than a conventional Temoporfin solution. The highest photosensitizer concentration in the tumour was obtained already at 6 hours after injection (FIG. 2), whereas the highest levels in skin were reached within 2 hours after injection. The drug concentration in skeletal muscle peaked 5 hours after injection. In comparison to conventional Temoporfin solutions the tumour:skeletal muscle ratio is 2 times higher for liposomal formulation. To summarize these results, we can conclude that a photodynamic therapy in this murine model will be feasible after only 6-7 hours post injection. This would mean that the Drug Light Interval (DLI) is reduced when compared to the conventional mTHPC formulation, which is closer to 96 hours post injection, thus accelerating PDT in a clinical setting, making this form of cancer treatment even more comfortable and practicable, because injection and irradiation can take place on a single day.

EXAMPLE 5

Antitumor Activity of Liposomal m-THPC

HT29, a metastasizing human colorectal tumor cell line was used.

Cells were maintained as a monolayer culture in Dulbecco's modified Eagle medium (DMEM) completed with 10% heat-inactivated fetal calf serum, 100 µg/ml streptomycin, 100 i.U./ml penicillin, at 37° C., in 95% air and 5% $CO_2$.

1. Tumour Model

Six week old athymic female mice (NMRI, nu/nu) were inoculated subcutaneously into the right hind foot with $8 \times 10^6$ HT29 cells. 10 days later, as the tumour had reached a diameter of approx. 10 mm, the test substance was injected intravenously. Unless indicated otherwise, 6 mice per dose and per Drug-Light-Interval (DLI) were used. A dose of 0.05; 0.08; 0.1; 0.12 mg/kg was applied.

2. Photodynamic Treatment

Drug-light interval (DLI) of 6 h was used. Each animal was photoirradiated at 652 mm with 20 $J/cm^2$ at 100 $mW/cm^2$ using a diode laser.

3. Evaluation of PDT Effect

FIG. 3 shows the PDT effect 6 hours after intravenous injection (DLI) of mTHPC liposomal formulation. The mice carrying HT29 tumors were treated with various doses of drug (0.05, 0.08, 0.10 and 0.12 mg/kg) intravenously, and after waiting for the DLI each was irradiated at 20 $J/cm^2$ of 652 nm laser light. The PDT effect of this experiment is documented by photographs taken at different time period (before 24 hrs, post 24 hrs, 1 week, 2 weeks, 3 weeks and 4 weeks) in the FIG. 3. The mice treated with 0.10 and 0.12 mg/kg showed strong tumor necrosis, and completely destruction of tumor after 3 weeks of PDT treatment and no residual tumor cells could be detected.

FIG. 4 further illustrates the correlation of drug dose and level of radiation dose ($J/cm^2$) in the tissue and efficacy of PDT. FIG. 4 indicates that the complete destruction of tumor at the highest levels of mTHPC per wet weight of tissue treated for 20 $J/cm^2$. While complete tumor necrosis was observed in much lower drug doses by increasing the light dose to 100 $J/cm^2$ Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

TABLE 1 mTHPC recovery rate after G50 gel filtration.

| | Absorp. | Volume (µl) | A × Volume |
|---|---|---|---|
| Fraction 1 | 0.0000 | 175 | 0.0000 |
| Fraction 2 | 0.1285 | 175 | 22.4875 |
| Fraction 3 | 0.4367 | 175 | 76.4225 |
| Fraction 4 | 0.1111 | 175 | 19.4425 |
| Fraction 5 | 0.0251 | 175 | 4.3925 |
| Fraction 6 | 0.0058 | 175 | 1.0150 |
| Fraction 7 | 0.0050 | 175 | 0.8750 |

TABLE 1-continued mTHPC recovery rate after G50 gel filtration.

|  | Absorp. | Volume (µl) | A × Volume |
|---|---|---|---|
| Fraction 8 | 0.0015 | 175 | 0.2625 |
| Fraction 9 | 0.0000 | 175 | 0.0000 |
| Fraction 10 | 0.0000 | 175 | 0.0000 |
| Fractions total | 0.7137 | 175 | 124.8975 |
| Probe | 0.6278 | 200 | 125.5600 |
| Recovery rate (%) |  |  | 99.4724 |

TABLE 2

Lipid recovery rate after G50 gel filtration.

|  | kcps | Volume (µl) | kcps × Volume |
|---|---|---|---|
| Fraction 1 | 0.30 | 175 | 52.50 |
| Fraction 2 | 28.50 | 175 | 4987.50 |
| Fraction 3 | 88.10 | 175 | 15417.50 |
| Fraction 4 | 24.40 | 175 | 4270.00 |
| Fraction 5 | 4.10 | 175 | 717.50 |
| Fraction 6 | 2.30 | 175 | 402.50 |
| Fraction 7 | 1.20 | 175 | 210.00 |
| Fraction 8 | 0.80 | 175 | 140.00 |
| Fraction 9 | 0.60 | 175 | 105.00 |
| Fraction 10 | 0.80 | 175 | 140.00 |
| Fractions Total | 151.10 | 175 | 26442.50 |
| Probe | 121.90 | 200 | 24380.00 |
| Recovery rate (%) |  |  | 108.46 |

What is claimed is:

1. A pharmaceutical liposomal formulation for photodynamic therapy, which is stable to freeze-drying and reconstitution, comprising:
    a liposomal bilayer, said bilayer consisting substantially of synthetic phospholipids;
    a monosaccharide;
    a therapeutically effective amount of a hydrophobic photosensitizer, wherein said hydrophobic photosensitizer is temoporfin;
    wherein said monosaccharide is selected from the group consisting of fructose and glucose;
    wherein said synthetic phospholipids of said liposomal bilayer are dipalmitoyl phosphatidyl choline, and dipalmitoyl phosphatidyl glycerol, with a weight ratio of dipalmitoyl phosphatidyl choline to dipalmitoyl phosphatidyl glycerol of about 10:1; and
    wherein the weight ratio of phospholipids to monosaccharide is between 1:2 and 1:12.

2. The liposomal formulation according to claim 1 wherein the weight ratio of phospholipids to monosaccharide is 2 to 5.

3. The liposomal formulation according to claim 1 wherein the therapeutically effective concentration of the photosensitizer is from 0.0001 to 0.15 percent w/v.

4. The liposomal formulation according to claim 1 reconstituted with an aqueous fluid for pharmaceutical administration.

5. A pharmaceutical liposomal formulation for photodynamic therapy, which is stable without freeze-drying, comprising:
    a liposomal bilayer, said bilayer consisting substantially of synthetic phospholipids;
    a monosaccharide, selected from the group consisting of fructose and glucose;
    a therapeutically effective amount of a hydrophobic photosensitizer, wherein said hydrophobic sensitizer is temoporfin;
    wherein said synthetic phospholipids of said liposomal bilayer are dipalmitoyl phosphatidyl choline, and dipalmitoyl phosphatidyl glycerol with a weight ratio of dipalmitoyl phosphatidyl choline to dipalmitoyl phosphatidyl glycerol of about 10:1; and
    an pharmaceutically suitable excipient carrier.

6. The pharmaceutical liposomal formulation for photodynamic therapy, which is stable without freeze-drying according to claim 5, wherein said pharmaceutically suitable excipient carrier is an aqueous osmotic solution compatible with body fluids.

* * * * *